US006706187B1

(12) United States Patent
Okano et al.

(10) Patent No.: US 6,706,187 B1
(45) Date of Patent: Mar. 16, 2004

(54) PACKING MATERIAL FOR CHROMATOGRAPHY HAVING NOVEL CHARACTERISTIC AND METHOD FOR ISOLATION OF SUBSTANCE USING THE SAME

(75) Inventors: Teruo Okano, 6-12-12, Kounodai, Ichikawa-shi, Chiba 272-0827 (JP); Akihiko Kikuchi, Tokyo (JP); Yasuhisa Sakurai, Tokyo (JP); Hideko Kanazawa, Kanagawa (JP); Yoshikazu Matsushima, Kanagawa (JP)

(73) Assignee: Teruo Okano, Chiba (JP)

( * ) Notice: Subject to any disclaimer, the term of this patent is extended or adjusted under 35 U.S.C. 154(b) by 0 days.

(21) Appl. No.: 09/700,602

(22) PCT Filed: May 24, 1999

(86) PCT No.: PCT/JP99/02698

§ 371 (c)(1),
(2), (4) Date: Jan. 19, 2001

(87) PCT Pub. No.: WO99/61904

PCT Pub. Date: Dec. 2, 1999

(30) Foreign Application Priority Data

May 22, 1998 (JP) .......................................... 10-140722

(51) Int. Cl.[7] .............................................. B01D 15/08
(52) U.S. Cl. ..................... 210/635; 210/656; 210/198.2
(58) Field of Search ................................ 210/635, 656, 210/659, 198.2

(56) References Cited

U.S. PATENT DOCUMENTS 6,372,141 B1 * 4/2002 Okano et al. ................ 210/635

FOREIGN PATENT DOCUMENTS

| EP | 534016 | * 3/1993 | ............ 210/198.2 |
| JP | 06-262071 | 9/1994 | |
| JP | 07-005161 | 1/1995 | |
| JP | 7-318551 | * 12/1995 | ............ 210/198.2 |
| JP | 08-103653 | 4/1996 | |
| JP | 09-49830 | 2/1997 | |
| WO | WO98/33064 | * 7/1998 | ............ 210/198.2 |

OTHER PUBLICATIONS

"Temperature–Responsive Chromatography Using Poly(N–isoprpylacrylamide)–Modified Silica," Hideko Kanazawa et al., Analytical Chemistry, vol. 68, No. 1, Jan. 1, 1996.

"Effect of temperature upon the chromatography of proteins on porous glass, chemically coated with N–isopropylacrylamide copolymer," A.E. Ivanov et al., Journal of Chromatography A. 776 (1997) 75–80.

"Temperature–Responsive Liquid Chromatography. 2. Effects of Hydrophobic Groups in N–Isoproplyacrylamide Copolymer–Modified Silica," Hideko Kanazawa et al., Analytical Chemistry, vol. 69, No. 5, Mar. 1, 1997.

* cited by examiner

*Primary Examiner*—Ernest G. Therkorn
(74) *Attorney, Agent, or Firm*—Fish & Richardson P.C.

(57) ABSTRACT

To provide chromatographic packings whereby biological components, etc. which cannot be separated by either ion-exchange chromatography or reversed phase chromatography employed alone can be efficiently separated without deteriorating their activities. Use is made of a packing which contains a charged copolymer and makes it possible to change the effective charge density on the surface of a stationary phase by a physical stimulus while fixing a mobile phase to an aqueous system.

16 Claims, 4 Drawing Sheets

PACKING MATERIAL FOR CHROMATOGRAPHY HAVING NOVEL CHARACTERISTIC AND METHOD FOR ISOLATION OF SUBSTANCE USING THE SAME

REFERENCE TO RELATED APPLICATIONS

This application is a 371 of PCT/JP99102698 filed May 24, 1999.

TECHNICAL FIELD

This invention relates to a packing which contains a charged (co)polymer and makes it possible to change the effective charge density or hydrophilic/hydrophobic balance on the surface of a stationary phase in an aqueous system by an external signal (for example, temperature), and a novel separation method by which substances such as metal elements, drugs or biological components are chromatographically separated by using the packing.

BACKGROUND ART

There a great variety of liquid chromatography techniques depending on the combination of stationary phase with mobile phase and the interaction systems employed for the separation. Liquid chromatography is a highly important technique for separating metal elements, isolating and purifying drugs and separating peptides, proteins, nucleic acids, etc. in the field of biochemistry. In recent years, moreover, attempts have been made to apply recombinant proteins, etc. produced by bioengineering procedures, which have made remarkable advances, to medicines. Under these circumstances, there is a growing requirement for efficient separation methods for separating and purifying these products. Chromatographic techniques commonly employed at present involve ion-exchange chromatography, reversed phase chromatography, etc.

In ion-exchange chromatography, separation is carried out by using, as a stationary phase, an electrolyte on the surface of an insoluble carrier and irreversibly adsorbing counter ions contained in the mobile phase. As the carrier, silica, cellulose, dextran, styrene/divinylbenzene copolymer, etc. are widely employed. Carriers having ion-exchange groups (for example, sulfonate, quaternary ammonium) introduced thereinto are commercially available as ion exchangers. Solute dissociate into cations, anions and amphoteric ions depending on the hydrogen ion concentration in the solution. When this solution is passed through an ion-exchange column, each ion binds to the oppositely charged exchange group on the carrier surface competitively with solvent ions, thus causing distribution between the solution and the ion exchanger surface at a certain ratio. The migration rates through the column vary depending on the bond strength and separation is completed by utilizing this difference in the migration rate. The distribution can be modified by some methods. For example, it can be changed by controlling the concentration of the competitive ion species in the mobile phase. Alternatively, the extent of ionization of the ion-exchange group on the carrier surface may be varied by changing the hydrogen ion concentration in the solution. That is to say, it has been a practice in ion-exchange chromatography to separate solutes from each other by controlling the ionic strength or the hydrogen ion concentration in the mobile phase to thereby change the elution order of the solutes.

Reversed phase chromatography involves the use of a combination of a hydrophobic stationary phase and a polar mobile phase. Solutes are distributed between the mobile phase and the stationary phase depending on the degree of hydrophobicity. In this case, solutes are eluted also by changing the degree of hydrophobicity of the solvent in the mobile phase to thereby change the distribution between the mobile phase and the stationary phase. Since an organic solvent is employed as the solvent in the mobile phase, it is feared that the activities of the biological components to be separated might be caused to deteriorated thereby.

In short, solutes are eluted and separated from each other fundamentally by varying the solvent in the mobile phase both in ion-exchange chromatography and reversed phase chromatography. Accordingly, there is a risk that the activity of the target sample might be damaged by an acid or organic solvent employed in the elution.

When it is intended to separate substances from each other by two or more chromatographies, each chromatography should be independently carried out, since chromatographic mode varies from carrier to carrier. If it is possible to perform ion-exchange chromatography and reversed phase chromatography by using a single carrier and a single physical stimulus, separation could be completed at an elevated efficiency within a shorter period of time. Moreover, substances which cannot be separated from each other by the conventional techniques can be separated thereby.

There are a great variety of biological components including charged-ones and uncharged ones. In general, a compound capable of being ionized is retained, in an unionized state, in a hydrophobic packing owing to hydrophobic interaction. When ionized, however, the hydrophobic interaction with the hydrophobic packing is weakened. Ion-dissociatable compounds differing in the dissociation constant can be easily separated from each other owing to the ion-ion interaction with the use of an ion exchanger.

It is generally known that weakly acidic ion exchange resins and weakly basic ion exchange resins are suitable respectively for separating basic proteins and acidic proteins. It is thus expected that, by introducing ion-exchange substituents, ion-exchange chromatography based on ion-ion interactions becomes usable in separating various substances, which are similar to each other in hydrophobicity or molecular weight and thus cannot be separated exclusively by hydrophobic interactions, and biological molecules such as proteins and nucleic acid oligomers.

However, there has been known hitherto neither any carrier which is usable both in ion-exchange chromatography and reversed phase chromatography when employed alone under one physical stimulus nor one usable in efficiently separating various substances, which are similar to each other in hydrophobicity or molecular weight and thus cannot be separated exclusively by hydrophobic interactions, and biological molecules such as proteins and nucleic acid oligomers.

DISCLOSURE OF INVENTION

To solve the above-mentioned problems, the present inventors have conducted studies and developments from various viewpoints. As a result, they have successfully prepared a novel packing having ion-exchange function by copolymerizing poly(N-isopropylacrylamide)(PIPAAm) with positively charged dimethylaminopropylacrylamide (DMAPAAm) and found that this packing is usable both in reversed phase chromatography and ion-exchange chromatography, when temperature is properly controlled. They have furthermore found that use of the charged copolymer makes it possible to control the LCST of the polymer by regulating pH value. The present invention has been completed based on these findings.

The present invention relates to a method for separating substances characterized by chromatographically separating said substances with the use of a packing which contains a charged (co)polymer and makes it possible to change the effective charge density on the surface of a stationary phase by an external stimulus while fixing a mobile phase to an aqueous system.

The present invention further relates to a method for separating substances characterized by retaining the substances in a stationary phase made of a chromatographic packing chemically modified with a polyalkylacrylamide copolymer having amino, carboxyl, hydroxyl groups, etc., then changing the hydrophilic/hydrophobic balance on the surface of the stationary phase by the temperature gradient method wherein the external temperature is changed stepwise, and passing the substances through a single mobile phase to thereby separate the same.

The present invention furthermore relates to a chromatographic packing which contains a charged (co)polymer and makes it possible to change the effective charge density on the surface of a stationary phase by a physical stimulus.

In the chromatographic packing of the present invention, the charged state of ion-exchange groups on the surface of a carrier can be reversibly controlled by changing the surface structure of the stationary phase by an external physical stimulus such as a change in temperature. Namely, the present invention provides a stationary phase which makes it possible to perform two chromatographic modes, i.e., ion-exchange chromatography and reversed phase chromatography, at the same time with the use of a mobile phase which is a single aqueous solvent (aqueous mobile phase). Moreover, the present invention provides a carrier capable of arbitrarily controlling the charge of ion-exchange groups on the surface of the carrier (in the case of ion-exchange chromatography) or the hydrophilic/hydrophobic balance (in the case of the reversed phase chromatography). The term "aqueous solvent" as used herein means water alone or aqueous solutions containing inorganic salts but free from any organic solvent.

The present invention provides a carrier for separation and purification characterized in that separation is performed by controlling the charge of ion-exchange groups on the surf ace of the stationary phase by regulating the physical properties or structure around the ion exchange groups on the carrier surface by a physical stimulus, while fixing the mobile phase to an aqueous system. According to the present invention, when the external temperature is lower than the critical temperature, the ion-exchange groups appear on the surface of the carrier. Then the biological components to be separated undergo interaction with the ion-exchange groups followed by separation by the ion-exchange chromatography mode. When the external temperature is higher than the critical temperature, on the other hand, the surface charge is weakened and the carrier becomes more hydrophobic. Then, the biological components can be separated by the reversed phase chromatography mode. That is to say, the hydrophilic/hydrophobic balance on the surface of the carrier can be reversibly and arbitrarily changed by controlling the external temperature.

BEST MODE FOR CARRYING OUT THE INVENTION

Figure 1:
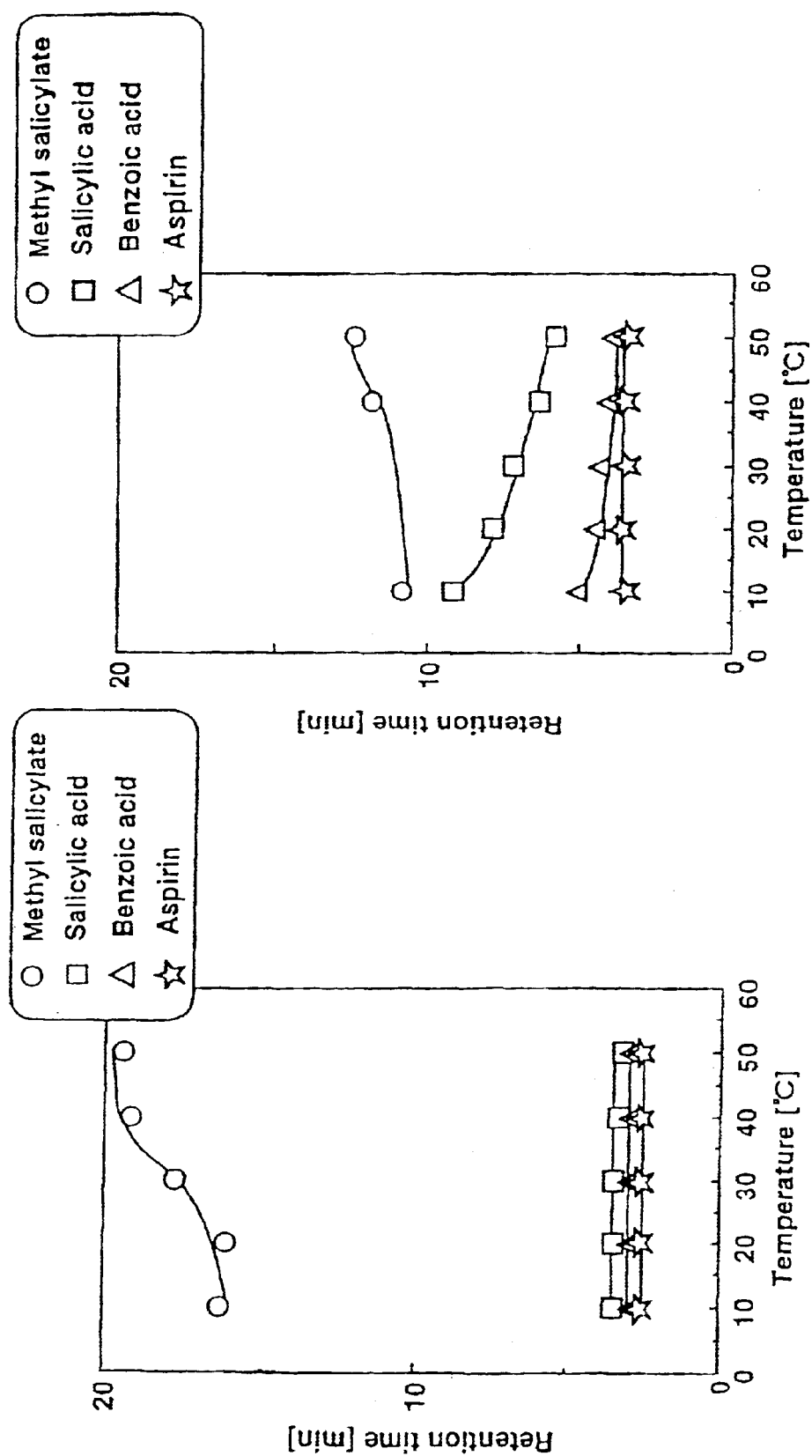
FIG. 1 provides graphs showing the relationship between temperature and retention time in the separation of aspirin, salicylic acid, methyl salicylate and benzoic acid with the use of two packings described in Example 2.

The external physical signal to be used in the method of the present invention is exemplified by a change in temperature. To alter the physical properties or structure around ion-exchange groups on the surface of the packing by changing temperature, for example, a temperature-responsive polymer may be introduced into the surface of the carrier. Examples of packings of this type include chromatographic packings chemically modified on the surface of the carrier with alkylacrylamide polymers or copolymers having amino, carboxyl, hydroxyl groups, etc. in the side chains or at the ends. Chemically modified packings are exemplified by silica carriers modified with the above-mentioned alkylacrylamide polymers or copolymers. To introduce ion-exchange groups, carriers may be chemically modified by copolymers of the above-mentioned alkylacrylamides-with comonomers having amino or carboxy groups.

Examples of the constitutional units of amino-containing polymers include dialkylaminoalkyl(meth)acrylamide, dialkylaminoalkyl (meth)acrylate, aminoalkyl (meth)acrylate, aminostyrene, aminoalkylstyrene, aminoalkyl (meth)acrylamide, alkyloxyalkyltrimethylammonium salts and (meth)acrylamido-alkyltrimethylammonium salts. Examples of the constitutional units of carboxyl-containing polymers include acrylic acid and methacrylic acid, while examples of the constitutional units of the sulfonate-containing polymers include (meth)acrylamido-alkylsulfonic acid.

It is preferable that the polyalkylacrylamide to be used in the present invention is selected from among poly(N-isopropylacrylamide), polydiethylacrylamide, poly(N-propylacrylamide) and polyacryloylpyrrolidine and copolymers of the constitutional units of these polymers with alkyl (meth)acrylate, as shown by the following formulae.

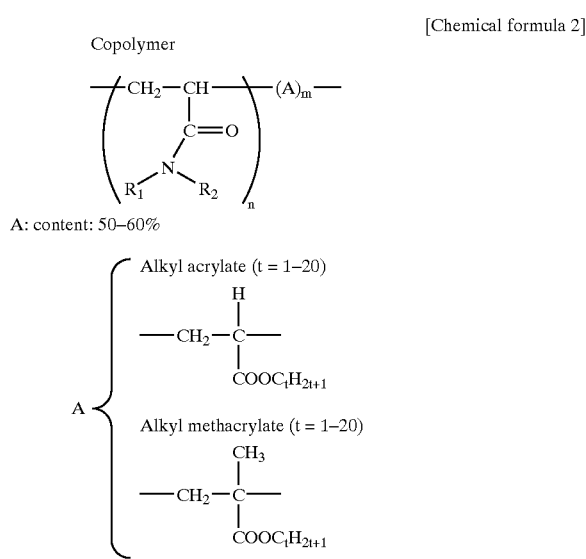

Since poly(N-isopropylacrylamide) has a lower limit of critical temperature of 32° C., a carrier chemically modified therewith undergoes a large change in the hydrophilic/hydrophobic surface properties at this critical temperature. When the surface of a chromatographic packing is grafted or coated with this polymer, the power of retaining a sample varies depending on temperature. Thus, the retention behavior can be regulated by controlling temperature without changing the composition of the eluate. A lower limit of critical temperature of 32° C. or above can be achieved by copolymerizing the N-isopropylacrylamide with comonomers which are more hydrophilic than isopropylacrylamide, for example, acrylamide, methacrylic acid, acrylic acid, dimethylacrylamide and vinyl pyrrolidone. On the other hand, a lower limit of critical temperature lower than 32° C. can be achieved by copolymerizing the N-isopropylacrylamide with hydrophobic comonomers, for example, styrene, alkyl methacrylate and alkyl acrylate.

The lower limit of critical temperature of polydiethylacrylamide is about 30 to 32° C. At this temperature, this polymer undergoes a change in the surface hydrophilic/hydrophobic nature. Similar to the above-mentioned case of poly(N-isopropylacrylamide), the power of retaining a sample can be thus regulated by controlling temperature. The novel chromatographic carrier to be used in the present invention is prepared by chemically modifying or coating the carrier with a polymer. The chemical modification can be carried out by two methods, i.e., surface grafting and radical polymerization. In the case of coating, on the other hand, the polymer is insolubilized within the application temperature range and then the insolubilized product is employed in coating.

As described above, surface grafting and radical polymerization can be employed as the chemical modification means by which a temperature-responsive polymer is introduced into a carrier. In the surface grafting method, a temperature-responsive polymer of a definite size is first synthesized and then grafted to the carrier. In the radical polymerization method, in contrast thereto, monomer(s) are polymerized on the surface of the carrier to give a polymer.

Compared with the surface grafting method, the radical polymerization method makes it possible to introduce the temperature-responsive polymer into the surface of the carrier at a high density. Thus, the hydrophobicity of the surface of the carrier can be elevated and the retention time can be easily controlled. In this case, moreover, non-specific adsorption on the carrier surface due to the interaction with silica gel can be easily suppressed.

Substances which can be separated by the method of the present invention include metal element ($Cu^{2+}$, $Mn^{2+}$, etc.), drugs (steroids, antipyretic analgesic agents, etc.) and biological components (peptides, proteins, nucleic acids, etc.). The method of the present invention is particularly useful in separating various biological components which cannot be separated by using either ion-exchange chromatography or reversed phase chromatography alone.

EXAMPLES

To further illustrate the present invention in greater detail, and not by way of limitation, the following Examples will be given.

Example 1

1. Synthesis of Polymer 1-1) Poly(IPAAm-DMAPAAm) (DMAPAAm:N,N-dimethylaminopropyl-acrylamide)

1-1-a) Preparation of IPAAm Copolymer Having Carboxyl End

An IPAAm copolymer having a carboxyl end was synthesized in such a manner as to give a molecular weight of 4,000 as a standard. The molecular weight of the polymer can be designed by controlling the amount of 3-mercaptopropionic acid (MPA) employed as a chain transfer agent. To prepare a copolymer having a molecular weight of 4,000, the amount of MPA was regulated so as to give a molar ratio MPA/(IPAAm+DMAPPAm) of 0.028.

| | |
|---|---:|
| Purified monomer IPAAM: | 25.0 g. |
| Cationic monomer (5% by mol of DMAPPAm based on IPAAm): | 1.72 g. |
| Radical polymerization initiator (2,2'-azobis (isobutyronitrile) (AIBN): | 0.145 g. |
| Chain transfer agent (3-mercaptopropionic acid): | 0.691 g. |
| DMF (N,N-dimethylformamide): | 50 ml. |

The above components were fed into a polymerization tube and fixed with a rubber ring provided with a three-way stopcock. The polymerization tube was introduced into liquid nitrogen, while closing the cock, and completely frozen. Next, the cock was opened and the contents of the tube were degassed by using a vacuum pump. After closing the cock again, the polymerization tube was introduced into methanol and the sample in the tube was completely dissolved. This procedure was repeated thrice (freezing/thawing degassing method). Then the polymerization tube containing the completely degassed sample under reduced pressure was introduced into a thermostat under shaking at 70° C., and radical polymerization was performed for 2 hours to thereby synthesize a copolymer having a carboxyl group at one end. After the completion of the reaction, the reaction mixture was cooled to room temperature by allowing to stand. Then the solvent (DMF) was concentrated by distilling at 40° C. under reduced pressure and the residue was dropped into ice-cooled diethyl ether to thereby give a polymer. The polymer thus obtained was taken up by filtration and dried at ordinary temperature under reduced pressure overnight. The dried product was dissolved in acetone and purified again with diethyl ether. The polymer thus obtained was taken up again by filtration and dried at ordinary temperature under reduced pressure overnight. The obtained polymer was then dissolved in purified water to give a 5% (w/v) solution. The resultant solution was transferred onto a dialysis membrane of a fractional molecular weight of 500 and dialyzed for 3 days. Thus a highly pure copolymer having a uniform molecular weight could be obtained.

1-1-b) Introduction of IPAAm Copolymer into Carrier (a) Active Esterification (Succinylation) Method To succinylate the copolymer synthesized above, the molar ratio of the copolymer: N,N'-dicyclohexylcarbodiimide (DCC): N-hydroxysuccinimide was adjusted to 1:2.5:2.

The copolymer was fed into a round-bottomed flask and dissolved in a half amount (25 to 30 mL) of ethyl acetate. Next, N-hydroxysuccinimide and DCC were added thereto followed by dissolution in the residual ethylacetate. The obtained mixture was immersed in ice-water at 4° C. and stirred with a stirrer for 2 hours. Subsequently, it was introduced into a thermostat at 25° C. and stirred therein overnight. The solution was filtered and thus dicyclohexyl urea formed as a by product was removed therefrom. After concentrating under reduced pressure, the residue was purified with diethyl ether. The product thus obtained was taken up by filtration and dried under reduced pressure. The succinylated copolymer thus obtained was stored in a freezer.

1-1-c) Introduction into Carrier (Silica Gel)

The succinylated copolymer was reacted in three portions with aminopropyl silica gel with the use of 1,4-dioxane as a solvent. The reaction was carried out at room temperature (25° C.). First, the succinylated polymer (1.0 g) was dissolved in 1,4-dioxane (50 mL) and reacted with aminopropyl silica gel (3 g) in a thermostat under shaking overnight. Subsequently, the liquid reaction mixture was filtered and the precipitate thus obtained and fresh copolymer (1.0 g) were dissolved in 1,4-dioxane (50 mL) again and reacted overnight. After repeating this procedure once again, the product finally taken up by filtration was sufficiently washed with methanol (500 mL) and distilled water (2 mL), dried under reduced pressure and then stored in a desiccator as a packing.

Example 2

1-2) Preparation of PIPAAm Hydrogel Surface 1-2-a) Formation of Gel Layer on Aminopropyl Silica Gel Surface To introduce a polymerization initiator into aminopropyl silica gel, the following compounds were used.

| | |
|---|---|
| Aminopropyl silica gel: | 5 g. |
| V-501: | 3.5 g (12.5. mmol). |
| EEDQ: | 6.18 g (25.0 mmol). |
| DMF: | 50 ml. |

Use was made of V-501 [4,41-azobis(4-cyanovaleric acid) (molecular weight: 280.28)] as a polymerization initiator and EEDQ [N-ethoxycarbonyl-2-ethoxy-1,2-dihydroquinoline, molecular weight: 247.30] as a condensing agent each in the amount as specified above. These compounds were reacted with aminopropyl silica gel in DMF. After bubbling $N_2$ gas thereinto in the dark for 30 minutes, the reaction vessel was completely charged with $N_2$ and reaction was carried out by using an $N_2$ balloon at room temperature for 6 hours. After the completion of the reaction, the mixture was filtered and washed with DMF. Thus, the polymerization initiator:had been introduced into the surface of the aminopropyl silica gel.

1-2-b) Formation of Surface Gel Layer

| | |
|---|---|
| Silica gel having V-501 bonded thereto prepared in above 1-2-a): | 4 g. |
| IPAAm: | 10 g. |
| BIS: | 0.27 g. |
| EtOH: | 200 ml. |
| DMAPAAm: | such an amount as to give a molar ratio to IPAAm of 8:2 or 9:1. |

Silica gel, IPAAm, DMAPAA and BIS [N,N'-methylene-bis (acrylamide), molecular weight: 154.17] were dissolved in ethanol. After bubbling $N_2$ gas thereinto in the dark for 1 hour, the reaction vessel was completely charged with $N_2$ and reaction was carried out in an oil bath at 70° C. by using an $N_2$ balloon for 5 hours, thus forming a gel layer on the surface of PIPAAm. After the completion of the reaction, the mixture was filtered and washed with methanol and water. The obtained product was dried under reduced pressure and stored in a desiccator as a packing. It was packed into a stainless column and employed in analysis.

Example 3

Aspirin, salicylic acid, methyl salicylate and benzoic acid were separated under the following conditions by using columns packed with a positively charged gal (IPAAm:DMAPAAm=8: 2) and IPAAm hydrogel.

Separation Conditions

Column: (1) packed with poly(IPAAm) hydrogel-modified silica;
(2) packed with poly(IPAAm-co-DMAAAm) (8:2) hydrogel-modified silica.

Buffer: $Na_2CO_3/NaHCO_3$.

pH=9.0.

Ionic strength=0.1 M.

FIG. 1 shows the results. Aspirin could not be separated from benzoic acid by using the column packed with the IPAAm hydrogel. In contrast, these compounds could be separated from each other by using the column packed with the positively charged gel (IPAAm: DMAPPAAm=8:2). At 10° C., in particular, all of the four compounds including charged and uncharged ones could be separated from each other within a short period of time of about 20 minutes. The order of separation depended on the hydrophobicity degrees of these compounds. In the cases of salicylic acid and benzoic acid, the retention times were shortened as temperature was elevated. This is seemingly because, when temperature was elevated, the structure and physical properties of the temperature-responsive polymer were changed and the charge on the carrier surface was thus lowered so as to reduce the interactions between the surface and the solutes. On the contrary, methyl salicylate (i.e., an uncharged compound) showed an prolonged retention time as temperature was elevated. This is seemingly because the temperature-responsive polymer became hydrophobic due to increase in temperature.

Example 4

Effects of pH Change

Figure 2:
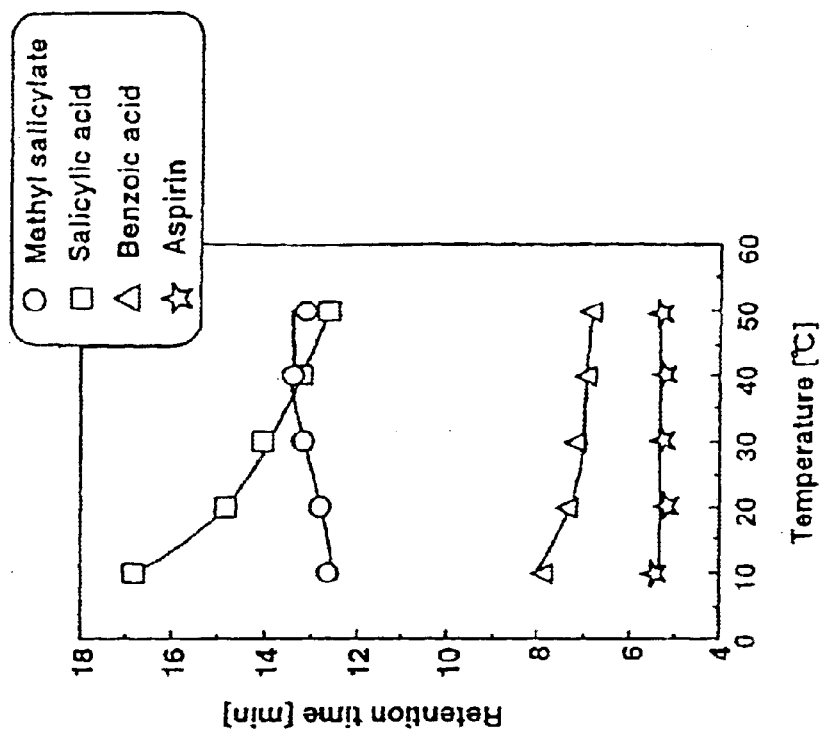
FIG. 2 provides graphs showing the relationship between temperature and retention time in the separation of aspirin, salicylic acid, methyl salicylate and benzoic acid while changing pH value in Example 3.
Figure 2:
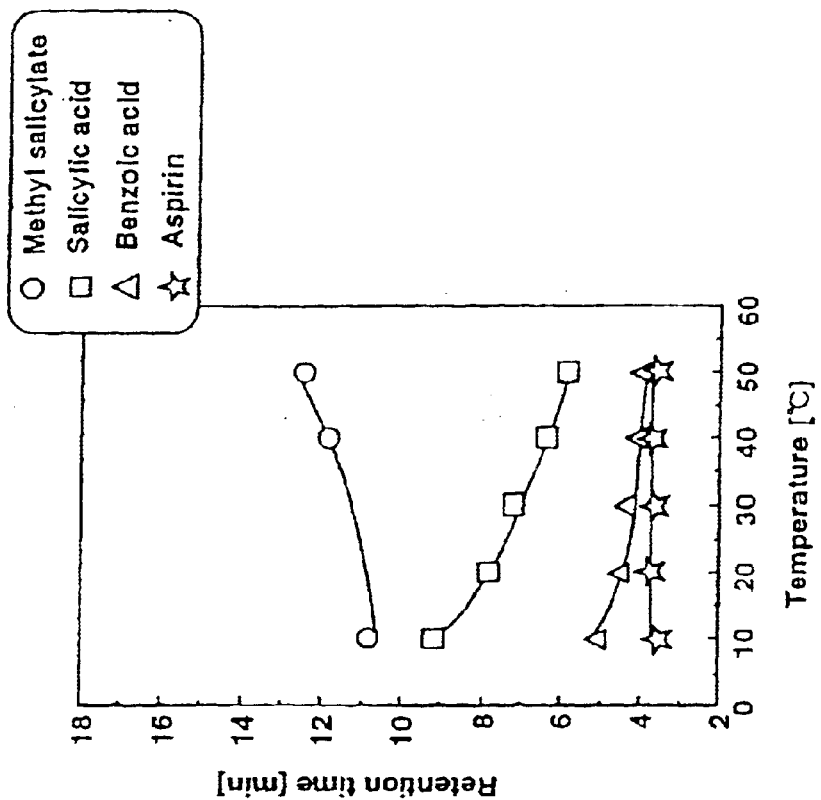

Aspirin, salicylic acid, methyl salicylate and benzoic acid were separated by the same method as the one of Example 3 but using the column packed with poly(IPAAm-co-dMAPAAm) (8:2) hydrogel-modified silica of Example 3 and $NaHPO_4/H_3C_6H_5O_7$ [citric acid $H_2O$ (monohydrate)] as a buffer at pH 7.0. FIG. 2 shows the results.

FIG. 2 indicates that the retention times of all of the substances were prolonged at pH 7.0, compared with at pH 9.0. This is seemingly because anionic compounds would undergo stronger interactions with the positively charged carrier surface at pH 7.0. These results suggest that the retention times of substances to be separated can be controlled by regulating pH value.

Example 5

Effects of Ionic Strength

Aspirin, salicylic acid, methyl salicylate and benzoic acid were separated by using a column packed with the poly(IPAAm-co-DMAPAAm) (8:2) hydrogel-modified silica of Example 3 under the following separation conditions.

Separation Conditions

Buffer: $NaHPO_4/H_3C_6H_5O_7$.
pH=7.0.
Ionic strength=1.0 M and 0.1 M.

Figure 3:
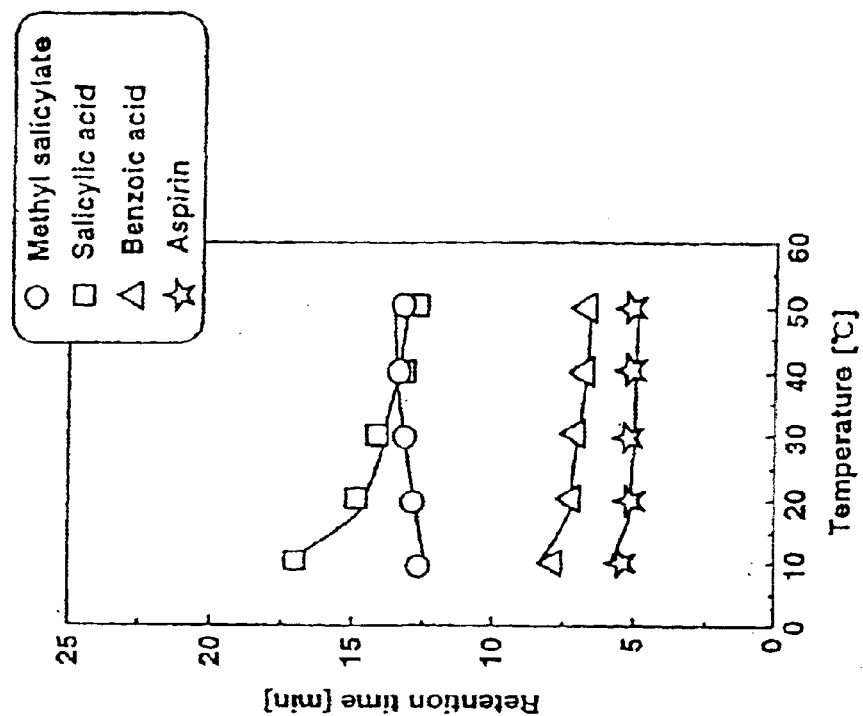
FIG. 3 provides graphs showing the relationship between temperature and retention time in the separation of aspirin, salicylic acid, methyl salicylate and benzoic acid while changing ionic strength in Example 4.
Figure 3:
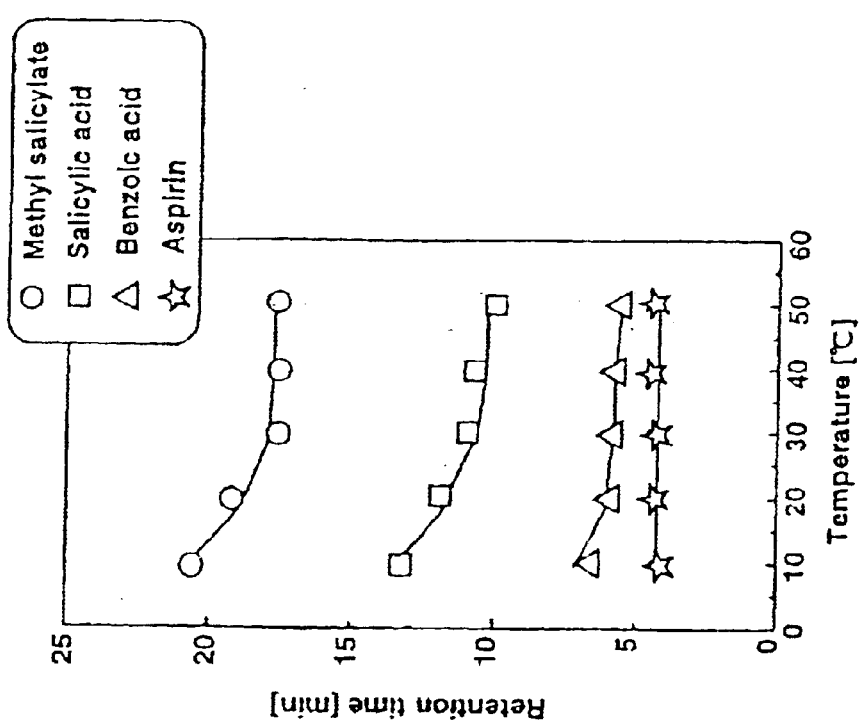

FIG. 3 shows the results. As the ionic strength was elevated (0.1 M→1.0 M), the retention times of all of the compounds but the uncharged methyl salicylate were shortened, while the retention time of methyl salicylate was prolonged. This is seemingly because, when the ionic strength was elevated, the protonation of amino groups on the surface of the carrier was suppressed and the positive charge was lowered, which weakened the interactions of the carrier surface with the anionic compounds. In the case of methyl salicylate, the hydrophobicity was elevated with an increase in the ionic strength and, in its turn, the hydrophobic interaction was seemingly strengthened.

Example 6

Effect of Polymerization Ratio of IPAAm to DMAPAAm

Aspirin, salicylic acid, methyl salicylate and benzoic acid were separated under the following conditions.

| Separation conditions | |
|---|---|
| Column: | (1) packed with poly(IPAAm-co-DMAPAAm) (9:1) hydrogel-modified silica; (2) packed with poly(IPAAm-co-DMAPAAm) (8:2) hydrogel-modified silica. |
| Buffer: | $NaHPO_4/H_3C_6H_5O_7$. |
| pH = | 7.0. |
| Ionic strength = | 0.1 M. |

Figure 4:
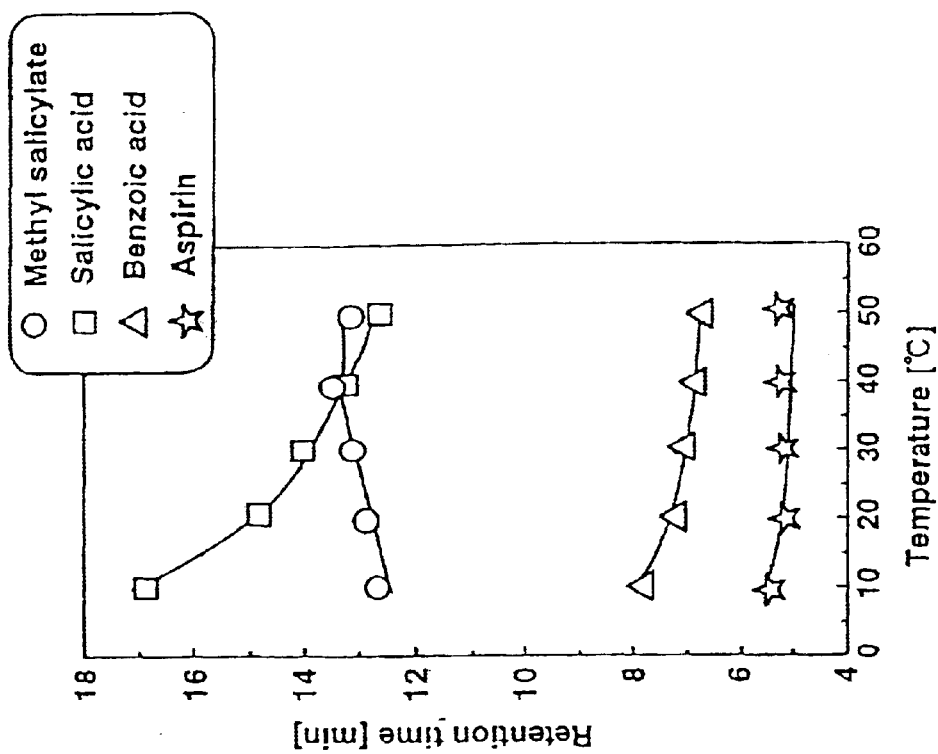
FIG. 4 provides graphs showing the relationship between temperature and retention time in the separation of aspirin, salicylic acid, methyl salicylate and benzoic acid while changing the polymerization ratio of IPAAm to DMAPAAm in Example 5.
Figure 4:
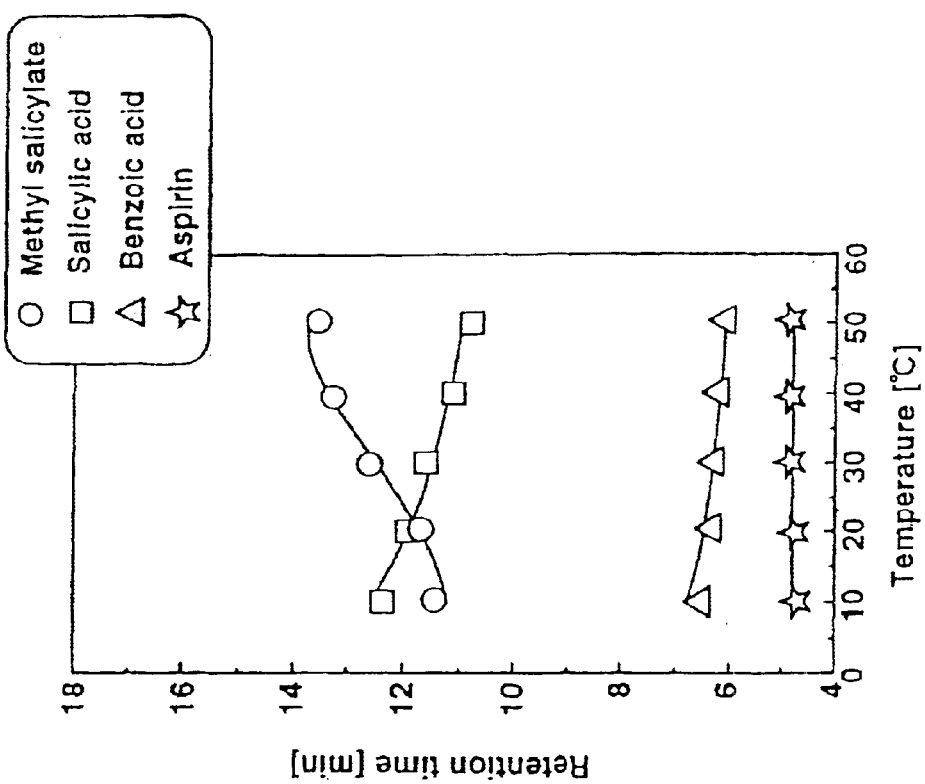

FIG. 4 shows the results. The retention times were prolonged with an increase in the ratio of the positively charged polymer, which indicates that retention time can be controlled by regulating the polymerization ratio.

Industrial Applicability

The present invention has the following advantages.

1) The charge of an ion exchanger exposed on the surface of the carrier can be arbitrarily controlled by regulating temperature. Thus separation can be performed in a single aqueous mobile phase without changing the solvent in the mobile phase.

2) Due to differences in hydrophobicity and ionic properties, separation can be carried out by a single operation. Compared with the conventional methods wherein two separating operations are needed, therefore, the method of the present invention is a highly efficient one and gives an elevated yield.

3) the method of the present invention makes it possible to separate biological components which cannot be separated by either ion-exchange chromatography or reversed phase chromatography employed alone.

4) since neither any acid nor organic solvent is used in the method of the present invention, biological components can be separated without deteriorating their activities.

5) compared with the conventional ion exchangers, the packing of the present invention can be quickly regenerated.

What is claimed is:

1. A method for separating substances characterized by chromatographically separating said substances with the use of a packing which contains a (co)polymer having a charged group in a side chain or at an end and makes it possible to change the effective charge density on the surface of a stationary phase by a physical stimulus while fixing a mobile phase to an aqueous system.

2. The separation method as claimed in claim 1, wherein said physical stimulus is a change in temperature.

3. The separation method as claimed in claim 2, wherein said packing is a chromatographic packing chemically modified on the surface of a carrier with a temperature-responsive polymer.

4. The separation method as claimed in claim 3, wherein said packing is a chromatographic packing chemically modified with a temperature-responsive polymer by using a radical polymerization method.

5. The separation method as claimed in claim 3 wherein said temperature-responsive polymer, with which the surface of the carrier is chemically modified, is a polyalkylacrylamide polymer or copolymer having an amino group, a carboxyl group, or a hydroxyl group in the side chains or at the ends.

6. The separation method as claimed in claim 5, wherein said polyalkylacrylamide is one selected from among poly(N-isopropylacrylamide), poly(N-propylacrylamide), polydiethylacrylamide and polyacryloylpyrrolidine.

7. The separation method as claimed in claim 1, wherein said substances are those selected from among metal elements, drugs and biological components.

8. A method for separating substances characterized by retaining the substances in a stationary phase made of a chromatographic packing chemically modified with a polyalkylacrylamide copolymer having an amino group in a side chain or at an end, a carboxyl group, or a hydroxyl group, then changing the hydrophilic/hydrophobic balance on the surface of the stationary phase by a temperature gradient method wherein an external temperature is changed stepwise, and passing the substances through a single mobile phase to thereby separate the same.

9. The separation method as claimed in claim 8, wherein said mobile phase is an aqueous solvent.

10. The separation method as claimed in claim 8, wherein said polyalkylacrylamide is one selected from among poly(N-isopropylacrylamide), poly(N-propylacrylamide), polydiethylacrylamide and polyacryloylpyrrolidine.

11. The separation method as claimed in claim 8, wherein said substances are those selected from among metal elements, drugs and biological components.

12. The separation method as claimed in claim 8, wherein the polyalkylacrylamide copolymer has a plurality of amino groups, a plurality of carboxyl groups, or a plurality of hydroxyl groups.

13. A method for separating substances characterized by chromatographically separating said substances with the use of a packing which contains a charged (co)polymer and makes it possible to change the effective charge density on the surface of a stationary phase by a change in temperature while fixing a mobile phase to an aqueous system, wherein said packing is a chromatographic packing chemically modified on the surface of a carrier with a temperature-responsive polymer, with which the surface of the carrier is chemically modified, is a polyalkylacrylamide polymer or copolymer having a plurality of amino groups, a plurality of carboxyl groups, or a plurality of hydroxyl groups in the side chains or at the ends.

14. The separation method as claimed in claim 13, wherein said packing is a chromatographic packing chemically modified with a temperature-responsive polymer by using a radical polymerization method.

15. The separation method as claimed in claim 13, wherein said polyalkylacrylamide is one selected from among poly(N-isopropylacrylamide), poly(N-propylacrylamide), polydiethylacrylamide and polyacryloylpyrrolidine.

16. The separation method as claimed in claim 13, wherein said substances are those selected from among metal elements, drugs and biological components.

* * * * *